US006631528B2

United States Patent
Landry

(12) United States Patent
(10) Patent No.: US 6,631,528 B2
(45) Date of Patent: Oct. 14, 2003

(54) CRIB SAFETY SHEET/BLANKET

(76) Inventor: Jo-Ann C. Landry, 13985 Spoonbill St. North, Jacksonville, FL (US) 32224

( * ) Notice: Subject to any disclaimer, the term of this patent is extended or adjusted under 35 U.S.C. 154(b) by 0 days.

(21) Appl. No.: 10/115,896

(22) Filed: Apr. 5, 2002

(65) Prior Publication Data
US 2003/0154548 A1 Aug. 21, 2003

Related U.S. Application Data
(60) Provisional application No. 60/356,773, filed on Feb. 15, 2002.

(51) Int. Cl.[7] ................................................ A47G 9/04
(52) U.S. Cl. ................... 5/494; 5/496; 5/498; 5/499; 5/502; 5/923; 2/69.5; 128/872; 128/873
(58) Field of Search ................ 5/494, 496, 497, 5/498, 499, 500, 502, 922, 923; 2/69.5; 128/872, 873; 24/72.5

(56) References Cited

U.S. PATENT DOCUMENTS

| | | | | | |
|---|---|---|---|---|---|
| 429,894 A | * | 6/1890 | Doremus | .......................... | 5/502 |
| 1,964,271 A | * | 6/1934 | O'Dwyer | .................... | 128/873 |
| 2,342,069 A | * | 2/1944 | Wilkinson | ................... | 128/872 |
| 2,423,392 A | * | 7/1947 | Krogh | .......................... | 128/873 |
| 2,481,741 A | * | 9/1949 | Graves | ........................ | 128/873 |
| 2,503,427 A | * | 4/1950 | Waterworth | ................ | 128/873 |
| 2,563,501 A | * | 8/1951 | Sperling | ....................... | 128/872 |
| 2,596,547 A | * | 5/1952 | Guest | ........................... | 5/502 |
| 2,677,834 A | | 5/1954 | Moynihan | .................... | 128/872 |
| 2,702,385 A | * | 2/1955 | Goldberg | ....................... | 2/69.5 |
| 3,521,309 A | * | 7/1970 | Evans | ............................. | 5/494 |
| 3,739,399 A | * | 6/1973 | Sheahon | ........................ | 2/69.5 |
| 3,845,513 A | | 11/1974 | Hubner | ........................ | 2/69.5 |
| 3,854,156 A | * | 12/1974 | Williams | ........................ | 5/421 |
| 3,987,505 A | * | 10/1976 | Hickey | ........................... | 2/114 |
| 4,172,300 A | * | 10/1979 | Miller | ....................... | 2/69.5 X |

(List continued on next page.)

FOREIGN PATENT DOCUMENTS

| | | | | |
|---|---|---|---|---|
| CH | 658177 | * 10/1986 | ..................... | 5/502 |
| GB | 927094 | * 5/1963 | ..................... | 5/502 |

OTHER PUBLICATIONS

Gershman, Maurice, M.D. "Self–Adhering Nylon Tapes." Journal of AMA. Oct. 18, 1958; 168:7.*

*Primary Examiner*—Robert G. Santos
(74) *Attorney, Agent, or Firm*—Richard C. Litman

(57) ABSTRACT

A crib safety sheet/blanket with a fitted sheet portion having a front surface and a back surface two opposing ends defining pockets for snugly fitting the sheet to a mattress. A blanket is sewn along its midline to the center of the fitted sheet, defining two blanket halves. Mating strips of hook and loop fastening material are attached to the two halves of the blanket, so that an infant may be placed on the blanket with the two halves of the blanket wrapped around the infant and fastened to retain the infant in a supine position. A plurality of elastic straps may extend across the bottom of the fitted sheet and be removably secured to the side of the sheet with mating strips of hook and loop fastening material to retain the sheet on the mattress.

16 Claims, 4 Drawing Sheets

U.S. PATENT DOCUMENTS

| | | | | |
|---|---|---|---|---|
| 4,202,052 A | | 5/1980 | Bilanzich | 2/69.5 |
| 4,445,242 A | * | 5/1984 | Bowen | 5/923 X |
| 4,597,121 A | * | 7/1986 | Bouma | 5/494 |
| 4,627,363 A | * | 12/1986 | Jones | 5/923 X |
| 4,783,866 A | * | 11/1988 | Simmons et al. | 5/639 |
| 4,839,934 A | * | 6/1989 | Rojas | 5/502 |
| 4,858,259 A | * | 8/1989 | Simmons et al. | 5/644 |
| 4,878,258 A | * | 11/1989 | Casey | 5/502 X |
| 4,887,326 A | * | 12/1989 | O'Brien et al. | 5/644 X |
| 4,897,885 A | * | 2/1990 | Lunt | 2/69.5 |
| 4,937,904 A | * | 7/1990 | Ross | 5/497 |
| 5,046,204 A | * | 9/1991 | Mohler | 5/413 R |
| 5,084,929 A | * | 2/1992 | Staudinger | 5/494 |
| 5,168,590 A | * | 12/1992 | O'Sullivan | 5/490 |
| 5,243,724 A | * | 9/1993 | Barnes | 5/482 |
| 5,297,304 A | * | 3/1994 | O'Sullivan | 5/630 |
| 5,367,731 A | * | 11/1994 | O'Sullivan | 5/645 |
| D355,068 S | * | 2/1995 | Prendergast | D2/719 |
| 5,400,803 A | * | 3/1995 | Vines | 128/872 |
| 5,488,746 A | * | 2/1996 | Hudson | 5/500 |
| 5,557,817 A | * | 9/1996 | Haddock | 5/922 X |
| 5,572,757 A | * | 11/1996 | O'Sullivan | 5/636 |
| 5,722,094 A | * | 3/1998 | Ruefer | 2/69.5 |
| 5,852,827 A | * | 12/1998 | Lear | 2/69.5 |
| 5,996,147 A | * | 12/1999 | Trimble | 5/500 X |
| 6,009,576 A | * | 1/2000 | Gramme et al. | 5/413 R |
| 6,105,168 A | * | 8/2000 | Hazen | 2/69.5 |
| 6,243,896 B1 | * | 6/2001 | Osuna et al. | 5/502 |
| 6,286,163 B1 | * | 9/2001 | Trimble | 5/496 X |
| 6,301,729 B1 | | 10/2001 | Hall | 5/494 |

* cited by examiner

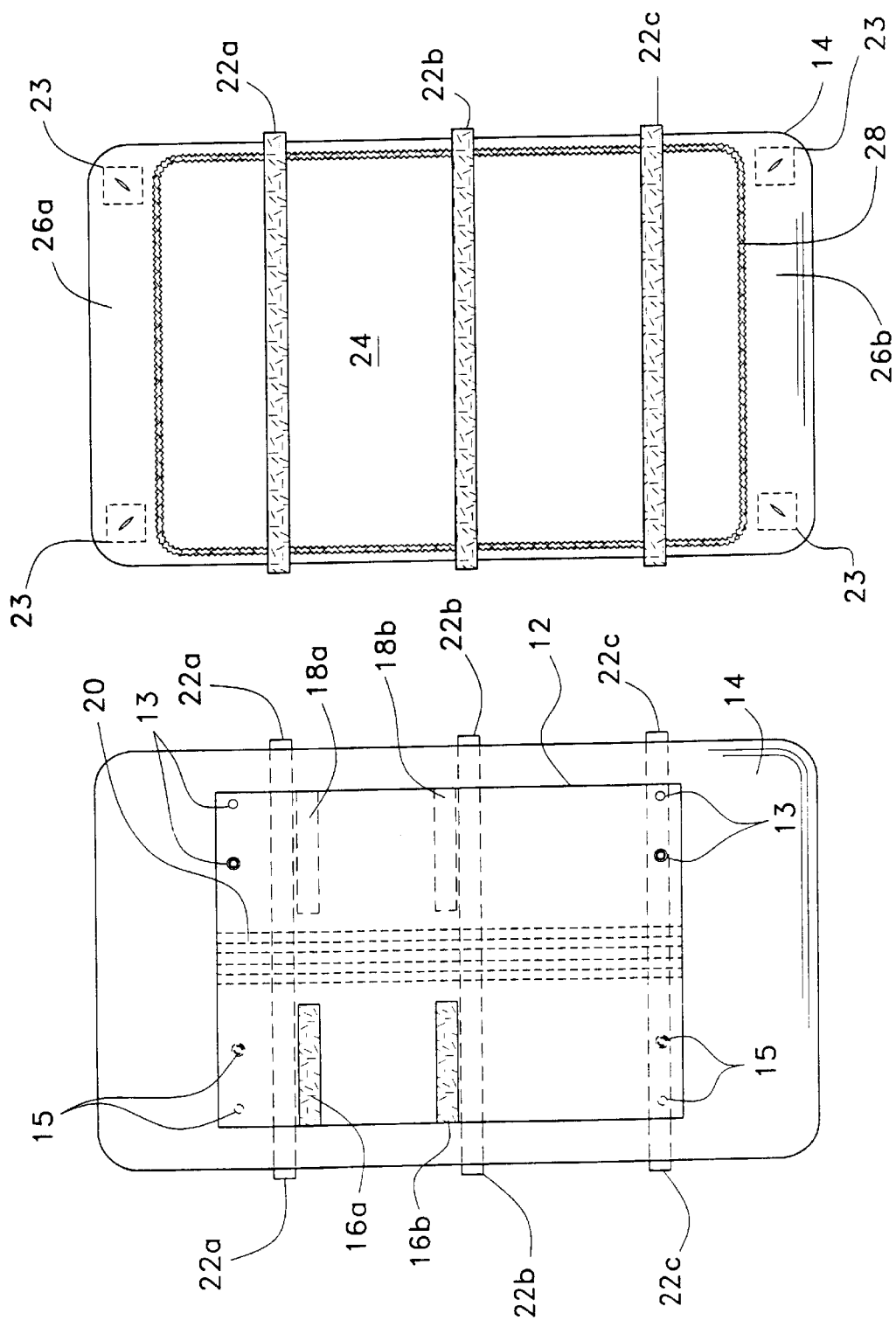

CRIB SAFETY SHEET/BLANKET

CROSS-REFERENCE TO RELATED APPLICATION

This application claims the benefit of U.S. Provisional Patent Application Ser. No. 60/356,773, filed Feb. 15, 2002.

BACKGROUND OF THE INVENTION

1. Field of the Invention

The present invention relates to sheets and blankets for an infant's crib or bed, and more particularly to an infant sheet and blanket combination adapted to secure an infant in a crib or bed.

2. Description of Related Art

There are a variety of infant blankets and coverings for infants present in the art. In the past many designs functioned only to keep an infant warm while sleeping. Today much more is known about infant sleeping patterns and sleeping safety. The concern for infant warmth is now shared with the concern for infant comfort and safety. Some infants frequently change positions while sleeping, so it is desirable to make an infant's sleeping enviroment as free as possible of suffocation hazards while at the same time insuring the infant is kept in a secure sleeping position.

An additional consideration in infant bedding design is Sudden Infant Death Syndrome (SIDS) in which an apparently healthy infant will expire in a crib for no apparent reason. While the causes of SIDS still remain somewhat a mystery it is thought that sleeping in the prone position may increase the likelihood of SIDS. A device to maintain an infant in the supine position while sleeping is therefore desirable.

U.S. Pat. No. 2,677,834 is typical of the earlier designs. The '834 patent discloses a crib blanket which is secured to the side of a crib with snap together fasteners. The blanket also contains a single strap along the blanket's upper margin for securing an infant to the blanket. This invention will keep a blanket secure in its relation to the crib but, unlike the present invention, uses only a single strap to secure the infant under the blanket. Further, the blanket is not attached to the crib sheet.

Other designs such as U.S. Pat. Nos. 3,845,513 and 4,202,052 disclose fitted garments which are sewn to crib sheets to restrict the movements of infants. The '513 patent shows a sleeping bag blanket secured to a bedlinen sheet, the baby being secured in the sleeping bag by a diaper retainer with button down flaps and by a pull down zipper. The '052 patent shows a sheet with a central pleat having an opening defined therein to which a jacket may be attached, the jacket being secured around the infant by what appear to be button or snap fasteners. No blanket is shown. Infants must be manipulated to be secured in these garment-type inventions, which often wakes the infant as he or she is being put to bed, a highly undesirable side effect.

U.S. Pat. No. 6,301,729 discloses one bedding device designed to prevent SIDS. It is a pocket like blanket device which secures an infant between one edge of the pocket and a mattress. This bedding device does not secure an infant in the same manner as the present invention however, nor does it permit an infant to be positioned on its side without the risk of the infant moving into the prone position while sleeping. The '301 invention also does not prevent an infant from squirming downward into the blanket pocket which could cause a suffocation hazard.

Therefore, it is desirable to have an infant bedding product which will function to keep an infant covered and warm, is as free as possible of suffocation hazards, is easy to use, is adjustable and will prevent an infant from moving into the prone sleeping position while still permitting some infant movement.

None of the above inventions and patents, taken either singly or in combination, is seen to describe the instant invention as claimed.

SUMMARY OF THE INVENTION

The crib sheet/blanket has a fitted sheet with a top surface, a bottom surface, and two opposing ends defining pockets for snugly fitting the sheet to a mattress. One end of at least two elastic straps is sewn to one side of the sheet. Hook and loop fastening material is attached to one side of the free end of each strap. Mating strips of hook and loop fastening material are attached to the other flat edge of the fitted sheet such that it may mate with the hook and loop fastening material on the straps.

Attached to the center of the sheet is a rectangular blanket with a front surface and a back surface. The blanket is sewn along a longitudinal midline to the fitted sheet, defining two blanket halves which may be wrapped around an infant. Strips of hook and loop fastening material are attached to each half of the blanket so that the blanket may be fastened around the infant to retain the infant in a supine position while sleeping.

An infant may be placed on its back or side in the center of the blanket attached to the sheet. The edges of the blanket are folded over the infant with one edge lying on top of the other edge. The edges are removably attached to one another with mating pieces of hook and loop fastening material. When secured by the hook and loop fasteners, the blanket functions to completely encircle the infant from just under the infant's arm pits to well past the infant's toes. The blanket is fastened securely enough to insure that the infant cannot roll into the prone position, but not so securely so as to preclude all movement of the infant.

Accordingly, it is a principal object of the invention to provide an infant crib blanket/sheet combination which can secure an infant in one position while still permitting some movement.

It is another object of the invention to provide an infant crib blanket/sheet combination which is a one piece design which will reduce suffocation hazards.

It is a further object of the invention to provide an infant crib blanket/sheet combination which will sufficiently insulate a sleeping infant.

It is still another object of this invention to provide an infant crib blanket/sheet combination which will allow an infant to be secured for sleeping with a limited amount of disturbance.

It is an additional object of this invention to provide an infant crib blanket/sheet combination which will secure an infant and at the same time allow quick and easy repeated access to that infant for monitoring and/or medical treatment.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2 is a top view of a crib safety sheet/blanket positioned around a mattress.

FIG. 3 is a bottom view of a crib safety sheet/blanket positioned around a mattress.

Similar reference characters denote corresponding features consistently throughout the attached drawings.

DETAILED DESCRIPTION OF THE PREFERRED EMBODIMENT

Figure 1:
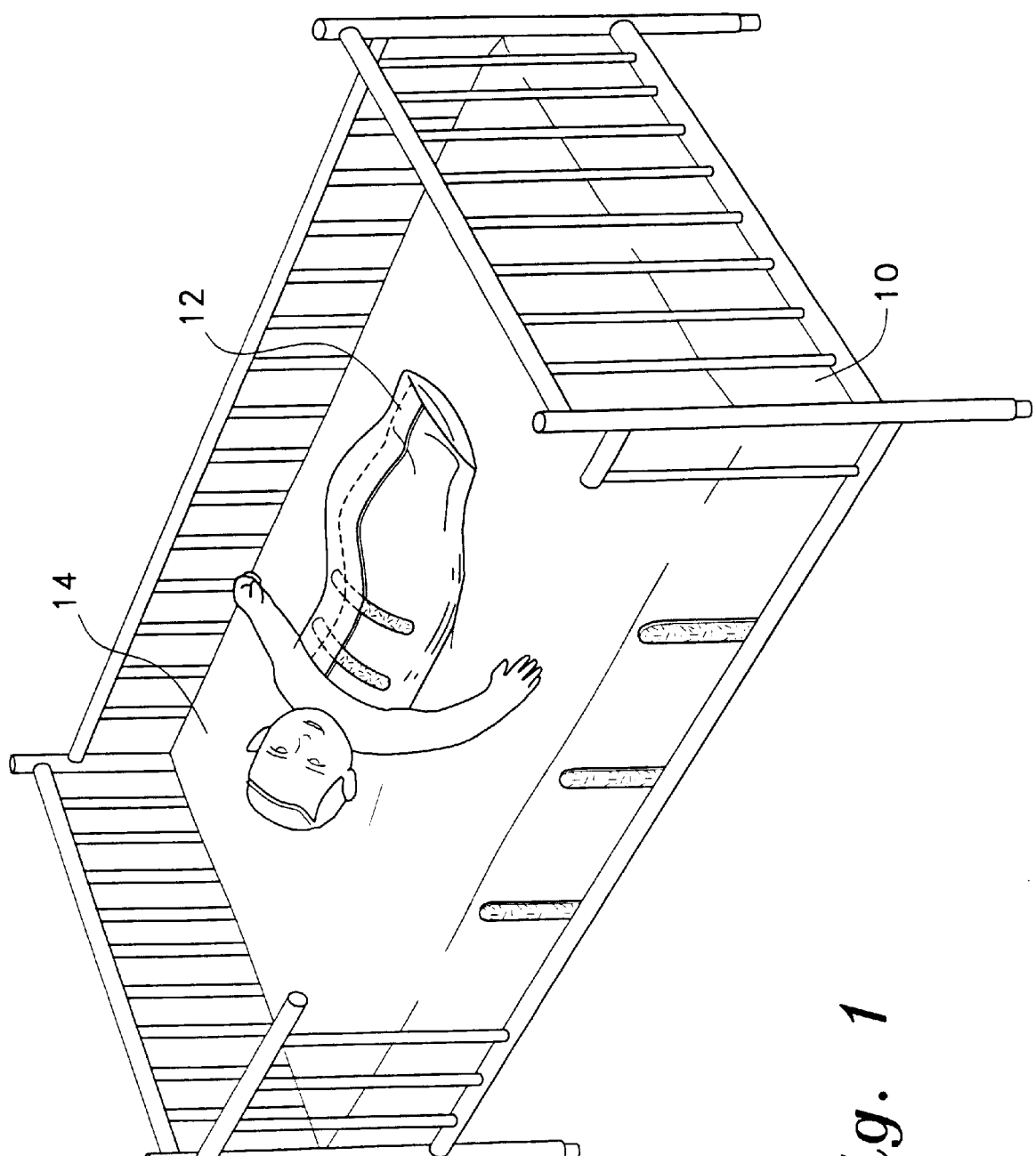
FIG. 1 is a fragmented, environmental, perspective view of a crib safety sheet/blanket according to the present invention with an secured infant secured in the blanket.

The first embodiment of the present invention is an infant crib safety sheet/blanket 10 which, as seen in FIG. 1, is installed on a mattress in a crib, bassinet, or the like. The invention has a blanket portion 12 (blanket) with a front surface and a back surface. The blanket is attached to a fitted sheet portion 14. The blanket 12 is preferably sewn to the middle of the front surface of the fitted sheet 14 by stitching along the longitudinal midline of the blanket portion 12, defining two halves of the blanket which may be folded or wrapped about the infant. When in use, the blanket 12 is wrapped around an infant's torso and lower extremities (with one side overlapping the other side) so as to keep the infant warm and securely positioned in the center of the safety sheet/blanket 10 on its back or side. The blanket 12 is held in position around the infant with four mating strips of hook and loop fastening material (discussed below).

When secured in the safety sheet/blanket an infant retains full motion in its arms and head and some lateral motion but is unable to roll completely over or to extract itself from the blanket 12. By securing an infant in this manner there is a lower chance of sudden infant death syndrome, which is normally associated with infants sleeping in the prone position. The infant has no loose bedding materials upon which to suffocate, and the infant cannot kick free of its blanket and become cold during sleep.

FIG. 2 is a top view of the safety sheet/blanket wrapped around a mattress with the blanket 12 laid flat against the sheet 14 and the back surface of the blanket 12 coming into contact with the front surface of the sheet 14. The stitching 20, which secures the blanket 12 to the sheet 14, can be seen in this view. The hook and loop fastening material 16a, 16b sewn to the front surface of the blanket 12 removably attaches to corresponding hook and loop fastening material 18a, 18b sewn to the back surface of the blanket 12. FIG. 2 shows two sets of mating hook and loop fasteners (16a with 18a, and 16b with 18b) but additional fastener strips may be attached and used if a more secure hold is required. FIG. 2 also shows the three elastic straps 22a–22c that wrap under the mattress (discussed below) to secure the flat edges of fitted sheet 14 to the mattress 24.

The blanket as seen in FIG. 2 may be adapted for smaller infants by folding the sides of the blanket to reduce the blanket's overall width. Preferably, the right side of the blanket would be folded toward the front surface of the blanket and fastened with snap fasteners 13 present thereon. The left side of the blanket would preferably be folded toward the back surface of the blanket and secured with snap fasteners 15 present thereon.

FIG. 3 is a bottom view of a safety sheet/blanket 10 wrapped around a mattress 24. This view shows the two pockets 26a, 26b defined in the fitted sheet 14 which secure the fitted sheet to the foot and head portions of a mattress 24.

An elastic band 28 functions to keep the two pockets 26a, 26b securely wrapped around a mattress. Three elastic straps 22a, 22b, and 22c keep side edges of the fitted sheet 14 secured to the mattress. The sheet 14 may have several cloth reinforced grommets 23 dispersed along the sides the sheet. These grommets 23 may serve as anchor points for bungee cords or other suitable holding devices when securing the crib sheet/blanket combination to the bed frame of a large bed so that the crib safety sheet/blanket 10 may be used when a crib is not available, e.g., when traveling.

Figure 4:
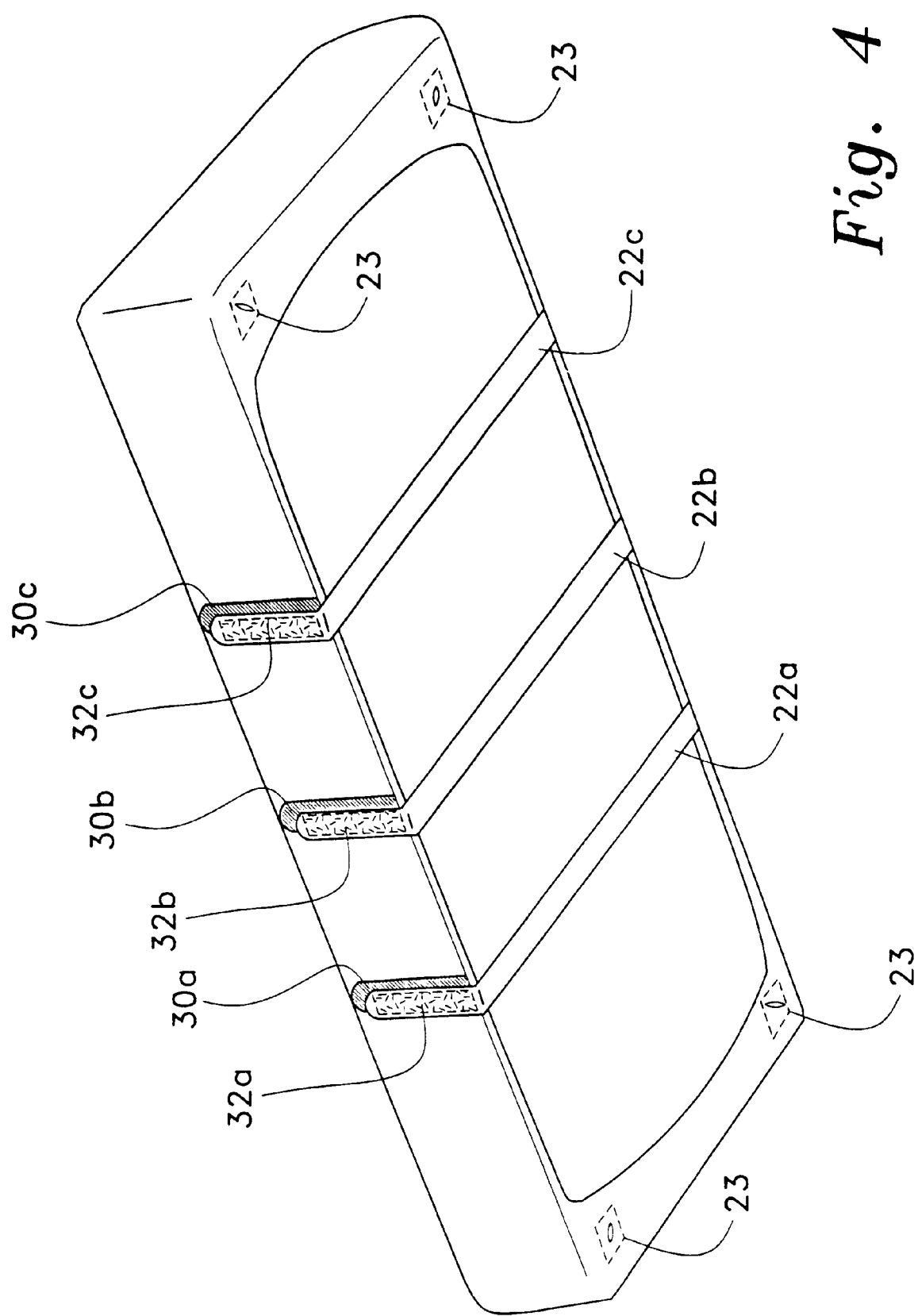
FIG. 4 is a perspective view of the bottom of a mattress equipped with an infant safety sheet/blanket.

FIG. 4 shows a perspective view of the bottom of safety sheet/blanket 10. The elastic straps 22a–22c are removably attached to one side of the fitted sheet 14, one strip of hook and loop fastening material 30a–30c for each strap 22a–22c being sewn to the fitted sheet 14 and a mating strip of hook and loop fastening material 32a–32c (seen in relief) being sewn to the elastic straps 22a–22c.

Figure 5:
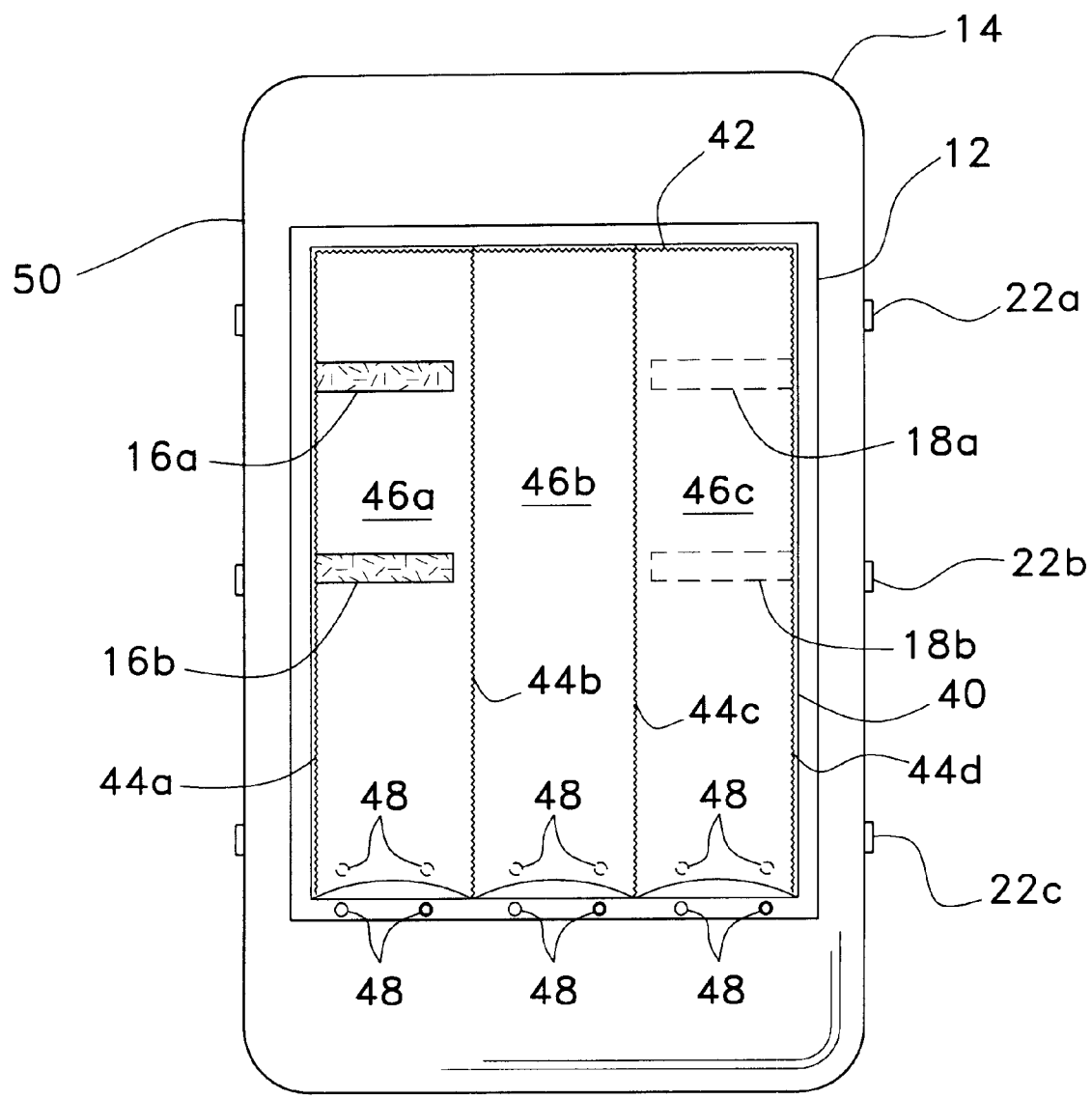
FIG. 5 is a top view of a second embodiment of the safety sheet/blanket positioned around a mattress.

FIG. 5 shows a second embodiment 50 of the safety sheet/blanket that is used for infants who need additional physical support while sleeping. This embodiment is similar to the first embodiment and the same reference numbers represent identical components.

The second embodiment of the safety blanket/sheet combination has a second blanket 40 with a top and bottom surface that is attached to the first blanket 12. The first blanket is shown larger in this figure for illustration purposes. One horizontal line of stitching 42 holds together the tops of both blankets and four vertical lines of stitching 44a–44d hold together the edges and the centers of the blankets. The four vertical lines of stitching 44a–44d also divide the blankets into three vertical sheaths 46a–46c. The bottoms of the sheaths 46a–46c may be closed using the snap fasteners 48 located on the bottom surface of the second blanket 40 and the top surface of the first blanket 12. Hook and loop fastening material, zippers, and any other fastening devices known to one skilled in the art may be substituted for the snap fasteners. Some of the hook and loop fastening material 16a, 16b has been moved in this embodiment to the top surface of the second blanket 40 from their position in the first embodiment on the top surface of the first blanket 12.

The second embodiment of the crib safety sheet/blanket combination is used in the same manner as the first embodiment except that supportive material such as egg-crate cushioning material or air pad-type material may be inserted into the sheaths 46a, 46b, 46c. Temperature regulating material such as hot and cold packs may also be inserted into the sheaths 46a, 46b, 46c. The supportive material is secured inside the sheaths by using the snap fasteners 48 located at the bottom of the sheaths.

It is well within the abilities of one skilled in the art to alter the shape and/or size of the fitted sheet and blanket to fit a variety of different infant sleeping devices such as cribs, bassinets, incubators and playpens. The sheet and the blanket may be made from any suitable material, including cotton, wool, polyester, silk and nylon.

It is to be understood that the present invention is not limited to the sole embodiment described above, but encompasses any and all embodiments within the scope of the following claims.

I claim:

1. A combination safety sheet/blanket for infants, comprising:

a fitted sheet having a top surface, bottom surface, a first side, an opposing second side, and two opposing ends, the ends defining pockets adapted for snugly fitting about opposing ends of a mattress;

a first blanket having a top surface, a bottom surface, a top edge a bottom edge a left side edge, a right side edge and a longitudinal mid-section, the mid-section of said first blanket being sewn to the top surface of said fitted sheet, defining first and second blanket halves;

blanket fastening means disposed on the top surface of said first blanket half and on the bottom surface of said second blanket half for temporarily fastening said first and second blanket halves of said first blanket together when said first and second blanket halves are placed in overlapping position with respect to one another to define a top opening along said top edge and a bottom opening along said bottom edge;

a plurality of straps, each of said straps having a first end and a second end, said first end being fixedly attached to the first side of said fitted sheet;

strap fastening means for removably attaching the second end of each of said straps to the second side of said fitted sheet;

whereby said fitted sheet may be secured to a mattress and said first and second halves of said blanket may be wrapped about an infant and secured by said blanket fastening means in order to retain the infant in a supine position while sleeping.

2. The combination safety sheet/blanket according to claim 1, where said blanket fastening means comprises mating strips of hook and loop fastening material disposed on the two halves of said blanket.

3. The combination safety sheet/blanket according to claim 1, where said strap fastening means comprises mating strips of hook and loop fastening material disposed on the second side of said fitted sheet and the first end of each said strap.

4. The safety sheet/blanket for infants according to claim 1, further comprising:

an elastic band disposed around the pockets of said fitted sheet.

5. The safety sheet/blanket according to claim 1, wherein said straps are made from an elastic material.

6. The safety sheet/blanket according to claim 1, further comprising:

a plurality of grommets disposed along the opposing sides of said sheet.

7. The safety sheet/blanket combination of claim 1, wherein:

said sheet and said blanket are made of materials selected from the group consisting of cotton, wool, polyester, silk and nylon.

8. The safety sheet/blanket combination of claim 1, further comprising a second blanket disposed upon said first blanket, wherein at least one sheath is defined between said first blanket and said second blanket.

9. The safety sheet/blanket combination of claim 8, wherein three sheaths are defined between said first and said second blanket.

10. The safety sheet/blanket combination of claim 8, further comprising supportive material inserted into the at least one sheath defined between said first and said second blanket.

11. The safety sheet/blanket combination of claim 10, wherein said supportive material is foam rubber.

12. The safety sheet/blanket combination of claim 10, wherein said supportive material is egg crate type foam rubber.

13. The safety sheet/blanket combination of claim 10, wherein said supportive material is a padding device utilizing trapped air.

14. The safety sheet/blanket combination of claim 10, wherein said supportive material is a cold pack.

15. The safety sheet/blanket combination of claim 10, wherein said supportive material is a hot pack.

16. The safety sheet/blanket combination of claim 1, further comprising snap fasteners, said snap fasteners being disposed at the bottom surface of said first blanket half and the top surface of said second blanket half for reducing the width of said first blanket.

* * * * *